United States Patent
Doughty

(10) Patent No.: US 7,123,361 B1
(45) Date of Patent: Oct. 17, 2006

(54) MICROPLASMA EMISSION SPECTROMETER

(75) Inventor: Frank C. Doughty, North Andover, MA (US)

(73) Assignee: Verionix Incorporated, North Andover, MA (US)

( * ) Notice: Subject to any disclaimer, the term of this patent is extended or adjusted under 35 U.S.C. 154(b) by 415 days.

(21) Appl. No.: 10/708,450

(22) Filed: Mar. 4, 2004

Related U.S. Application Data

(60) Provisional application No. 60/452,235, filed on Mar. 5, 2003.

(51) Int. Cl.
*G01J 3/30* (2006.01)

(52) U.S. Cl. ........................................... 356/316
(58) Field of Classification Search .............. 356/316
See application file for complete search history.

(56) References Cited

U.S. PATENT DOCUMENTS

| | | | |
|---|---|---|---|
| 4,575,241 A | 3/1986 | Demers et al. | 356/316 |
| 4,664,477 A | 5/1987 | Andrieu et al. | 356/316 |
| 4,820,048 A | 4/1989 | Barnard | 356/328 |
| 4,973,159 A | 11/1990 | Sohma et al. | 356/328 |
| 5,483,337 A | 1/1996 | Barnard et al. | 356/316 |
| 5,570,179 A | 10/1996 | Weckstrom | 356/311 |
| 5,596,407 A | 1/1997 | Zander et al. | 356/316 |
| 5,654,796 A | 8/1997 | Mundt | 356/316 |
| 5,942,855 A | 8/1999 | Hopwood | 315/111.51 |
| 5,986,747 A | 11/1999 | Moran | 356/72 |
| 6,043,881 A | 3/2000 | Wegrzyn et al. | 356/316 |
| 6,069,695 A * | 5/2000 | Rohr et al. | 356/318 |
| 6,381,014 B1 | 4/2002 | Platzer et al. | 356/316 |
| 6,429,935 B1 | 8/2002 | Duan | 356/316 |
| 6,538,734 B1 | 3/2003 | Powell | 356/316 |
| 6,577,390 B1 | 6/2003 | Efthimion | 356/316 |
| 6,594,010 B1 | 7/2003 | Malczewski et al. | 356/311 |
| 6,643,014 B1 | 11/2003 | Chevalier et al. | 356/316 |
| 2002/0071117 A1 | 6/2002 | Ukon et al. | 356/316 |
| 2002/0093652 A1 | 7/2002 | Powell | 356/316 |
| 2003/0214651 A1 | 11/2003 | Hudak | 356/316 |

OTHER PUBLICATIONS

Gaurand, et al. An Innovative Plasma Source For On Line process Monitoring, Alcatel Vacuum Technology France, Annecy, France.

* cited by examiner

*Primary Examiner*—Gregory J. Toatley, Jr.
*Assistant Examiner*—Kara Geisel
(74) *Attorney, Agent, or Firm*—Kurt Rauschenbach; Rauschenbach Patent Law Group, LLC

(57) ABSTRACT

A microplasma emission spectrometer is described that includes a chamber for confining a sample volume of gas. A microplasma source that includes a resonant antenna structure generates a microplasma in the chamber from the sample volume of gas. A RF power supply provides power to the resonant antenna structure that generates the microplasma from the sample volume of gas. A spectrally sensitive detector is optically coupled to the microplasma. The entrance of the spectrally sensitive detector has dimensions and is positioned so that emissions from at least one-tenth of a total volume of the microplasma are transmitted through the entrance of the spectrally sensitive detector.

39 Claims, 4 Drawing Sheets

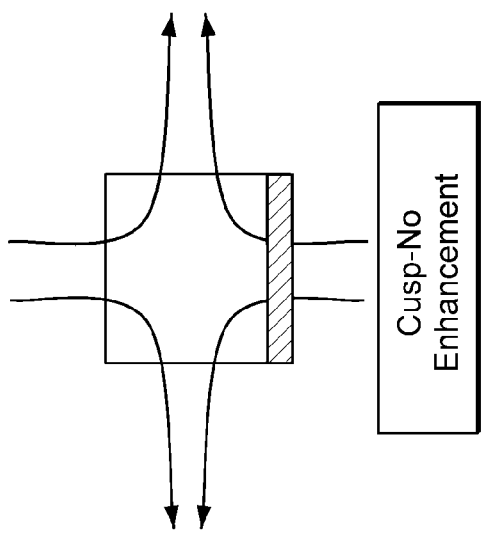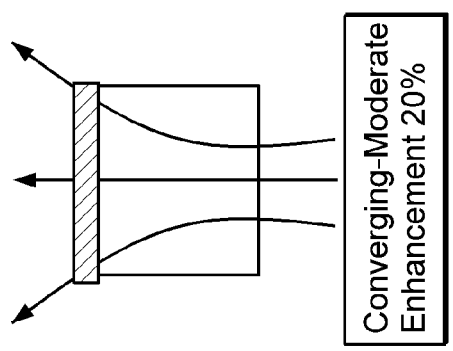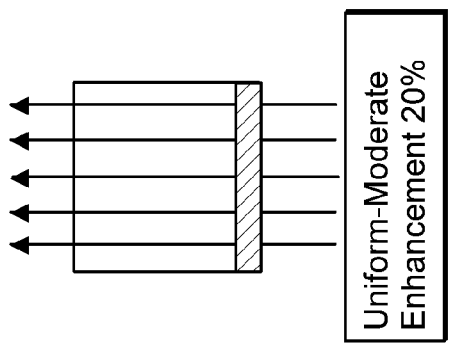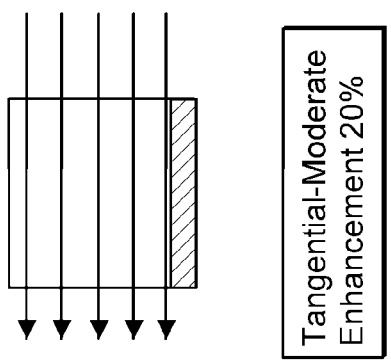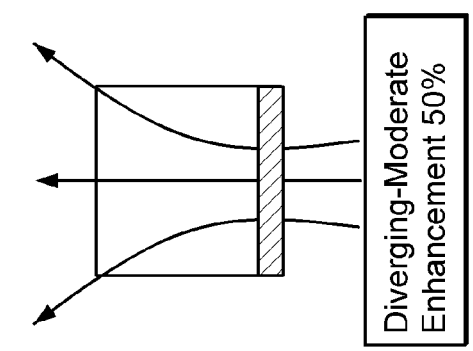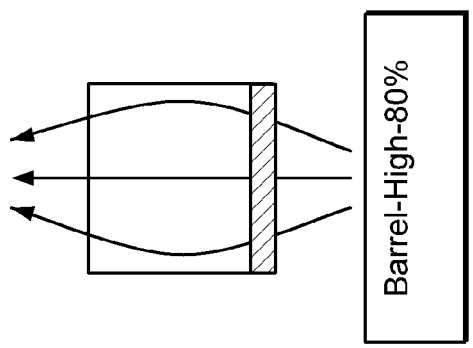

MICROPLASMA EMISSION SPECTROMETER

CROSS REFERENCE TO RELATED APPLICATIONS

This application claims priority to provisional patent application Ser. No. 60/452,235, filed on Mar. 5, 2003, the entire disclosure of which is incorporated herein by reference.

BACKGROUND OF INVENTION

Many industrial and scientific applications require chemical analysis of gas and liquid phase materials to obtain data for these applications. Also, many environmental applications require chemical analysis of gas and liquid phase materials to obtain data useful for health and safety analysis.

Numerous techniques and apparatus have been developed to perform chemical analysis of gas and liquid phase materials. One common analytical technique used for gas phase analysis is plasma emission spectrometry. Plasma emission spectrometry is performed by electrically exciting gas to form a plasma where one or more species undergo excitation and decay via emission at UV, visible, or infrared wavelengths. Detailed spectral analysis of these emissions can be used to determine the gas composition or the composition of liquid phase analytes that are volatilized into the gas stream. The spectral analysis can include ultraviolet and infrared spectral analysis depending upon the particular application.

One known method of performing plasma emission spectrometry uses a plasma torch to breakdown the material under test. Typical operating powers for the plasma torch are several kilowatts. Typical gas flow rates are on order of several liters/min. Such systems are relatively large having a footprint on the order of several cubic feet, which limits their application to laboratory installations.

BRIEF DESCRIPTION OF DRAWINGS

This invention is described with particularity in the Detailed Description and Claims sections. The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 4 illustrates various magnetic field configurations that provide magnetic field enhancements to the microplasma source.

DETAILED DESCRIPTION

Most known systems for performing chemical analysis have plasma sources that have relatively large dimensions, which typically are on order of 5–10 cm. The input power necessary to generate a plasma density in the W/cm$^3$ range for such a plasma source may be as high as several kilowatts. These known systems have several disadvantages. One disadvantage is that these systems are not suitable for portable operation with a battery powered power supply. Another disadvantage is that the power supplies in these systems are relatively large, complex and expensive.

In addition, these known systems for performing chemical analysis are relatively inefficient because the fraction of the optical emission generated that is actually coupled to the optical detector is typically very small due to the low numerical aperture of the optical collection systems. Thus, only a very small region, which is typically millimeter sized, is effectively imaged onto the spectrometer entrance slit and the electrical power input to optical emission output ratio is extremely low. Known spectrometer systems can not be easily scaled. Many of the components used to fabricate known spectrometer systems are difficult or impossible to fabricate at small scales.

The microplasma spectrometer of the present invention generates a relatively small and highly efficient plasma discharge that can be powered by commercially available RF power amplifier chips that consume only a few watts of total power. Consequently, the microplasma spectrometer of the present invention can be manufactured in a relatively small physical volume compared with known plasma spectrometers that perform similar functions and thus can be relatively inexpensive to manufacture and is suitable for many remote applications. Furthermore the microplasma spectrometer of the present invention has relatively low power dissipation and thus does not require cooling.

Figure 1:
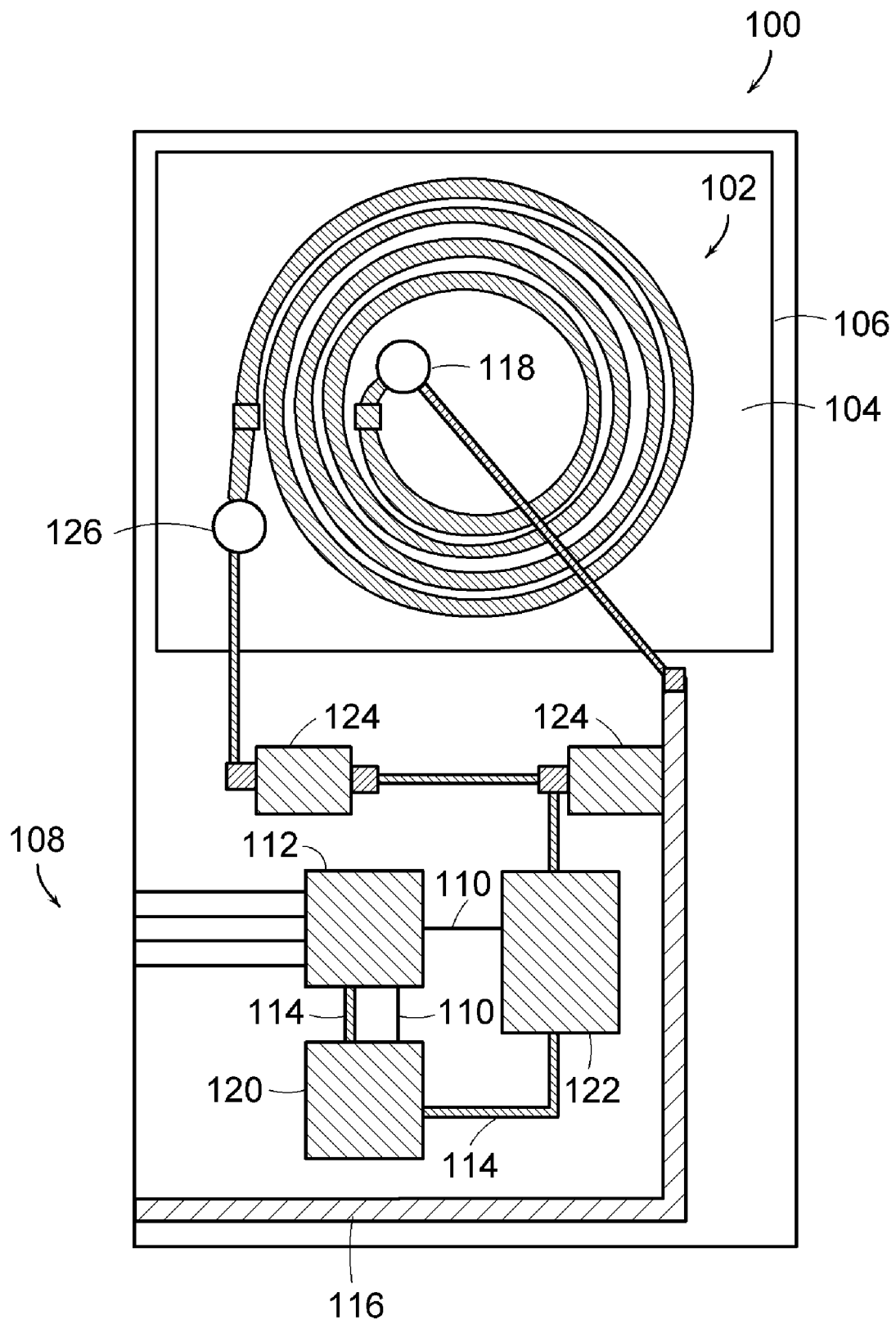
FIG. 1 is a block diagram of a top view of a microplasma source according to the present invention.

FIG. 1 illustrates a block diagram of a top view of a microplasma source 100 according to the present invention. The microplasma source 100 includes a high efficiency resonant antenna structure 102 that is positioned in proximity to an emission chamber (not shown). The resonant antenna structure 102 does not need to be in contact with a plasma generated by the microplasma source 100. In some embodiments, the resonant antenna structure is separated from the plasma by a protected layer, such as a substrate material, a window or a thin film. A high efficiency resonant antenna structure 102 is necessary for most practical applications because microplasmas are relatively small and thus subject to large wall or diffusional losses.

In one embodiment, the resonant antenna structure 102 is a discrete component that is mounted on a substrate or printed circuit board as one of several discrete components. For example, the resonant antenna structure 102 can be a discrete antenna structure that is formed of a high-conductivity material and then physically attached to a low-loss substrate 104. In other embodiments, the resonant antenna structure 102 is fabricated on a monolithic substrate with other monolithic components or in a hybrid assembly.

The antenna resonant structure 102 can be fabricated from numerous types of high-conductivity materials, such as copper. Copper is suitable for such structures, but is subject to corrosion and oxidation, which can vastly increase the resistance and change the properties of the antenna structure 102. Unprotected copper structures can have relatively short lifetimes in some environments. The copper surface may be protected by a thin coating of gold or solder, but this increases the series resistance of the antenna.

Alternately, the resonant antenna structure 102 can be formed of copper that is protected from oxidation and corrosion by a coating. Many protective coatings, such as polyimides, BCB (benzocyclobutene) or amorphous silicon oxides and nitrides can also be used to protect the copper from oxidation and corrosion. Loss properties at the drive frequency, long term stability, and the ability to protect the underlying metal are all important factors in choosing a protective coating. Other materials, such as gold, nickel, electro-less nickel, silver, tin, and a solder material can also be used to fabricate the discrete component antenna structure 102. The resonant antenna structure 102 can be attached to or fabricated on numerous types of low-loss substrates 104, such as FR-4, RF-35 and TLY-5 substrates, which are known in the industry. Using a low-loss substrate will reduce losses and power consumption and lower the operating temperature of the resonant antenna structure 102. These properties make the resonant antenna structure 102 more efficient and increase the optical emission signal and the utility of the system.

The dimensions of the resonant antenna structure 102 can be optimized for the operating pressure that is most suitable for the particular system application. For example, using a relatively large diameter antenna structure 102 can improve performance for relatively low pressure applications, such as analyzing gases in semiconductor processing equipment. Performance will be improved because the relatively large diameter antenna structure will result in a resonant frequency that is more closely coupled to the electron-neutral collision frequency of the low pressure gas.

A window 106 can be positioned over the top of the resonant antenna structure 102 and may be attached with a high-temperature, low-loss adhesive material. The window 106 can be formed of numerous types of materials, such as glass, quartz, or sapphire. The window 106 can form an inner surface of the chamber (not shown) that is used to contain the plasma. The window 106 also further protects the resonant antenna structure 102 from oxidation and corrosion. In system applications where the chamber is at a sub-atmospheric pressure, the window 106 may function as a vacuum window. In other applications, the window 106 may be a passivation window.

The microplasma source includes a DC power and control input 108 that is electrically connected to a DC power supply (not shown) and to a control circuit (not shown). The DC power and control input 108 provides DC power and control signals to active components in the microplasma source 100. The DC power and control input 108 is electrically connected to a DC power bus 110 that supplies power to the active components in the microplasma source 100.

The microplasma source 100 includes a RF signal generator 112 having an input that is connected to the DC power and control input 108 and an output that is electrically connected to a RF transmission line 114. The RF signal generator 112 generates a RF signal that propagates on the RF transmission line 114 which connects to the resonant antenna structure 102 at a first point 126. A ground bus 116 provides a DC and a RF return path. The ground bus 116 is electrically connected to a second point 118 on the resonant antenna structure 102.

A preamplifer 120 and a power amplifier 122 are electrically coupled by the RF transmission line 114. The preamplifer 120 and the power amplifier 122 amplify the RF signal generated by the RF signal generator 112 to the desired power level. In one embodiment, the DC power and control input 108 includes a power and frequency control signal input for controlling the power and frequency of the RF signal generated by the RF signal generator 112.

Impedance matching components 124 are attached or integrated into the substrate 104 and are electrically coupled into the ground bus 116 and into the RF transmission line 114. An output of the impedance matching component 124 that is coupled into the RF transmission line 114 is electrically connected to the first point 126 on the resonant antenna structure 102 through the RF transmission line 114. In one embodiment, the impedance matching components 124 are discrete capacitors that are electrically coupled into the ground bus 116 and into the RF transmission line 114.

The impedance matching components 124 are chosen to approximately match the input impedance of the resonant antenna structure 102 to the impedance presented by the RF signal transmission line 114 that couples the RF generator 112, the preamplifer 120 and the power amplifier 122. Matching the impedance can increase or maximize the power transferred to the resonant antenna structure 102 and will increase the efficiency of the microplasma source 100. High efficiency sources are useful for manufacturing miniaturized plasma systems that achieve high signal strengths at low overall power levels.

In one embodiment, the impedance matching components 124 are interdigitated capacitive structures that are integrated into the substrate 104. In another embodiment, the impedance matching components 124 are discrete board-mounted impedance matching components, such as chip capacitors that are electrically coupled into the ground bus 116 and the RF transmission line 114. Discrete board-mounted impedance matching components are typically significantly less expensive to manufacture and mount on a substrate relative to manufacturing integrated interdigitated capacitive structures on a monolithic substrate. Interdigitated capacitive structures have relatively fine manufacturing tolerance and therefore, are relatively expensive to manufacture.

In yet other embodiments, the impedance matching components 124 are not physically located on the substrate 104. In some embodiments, the microplasma source 100 includes connectors, such as coaxial connectors, that interconnect transmission lines, which allows the single board to be divided into multiple boards.

Many discrete impedance matching components have relatively high Q and, therefore, are suitable for use in a microplasma source. Equivalent series resistance and Q at the frequency of operation are critical parameters. Microplasma sources including discrete board-mounted impedance matching components can have relatively high emission intensity and, therefore, can be used to generate relatively high signal-to-noise ratio signals. A microplasma source constructed according to the present invention with a 3-turn resonant antenna structure having 0.015 in (0.375 mm) lines and spaces and a 5–10 mm diameter had an emission intensity that was approximately two times higher than known sources fabricated from conventional solder surface metallization on FR-4.

In some embodiments, the resonant antenna structure 102 is designed to be resonant at one particular fundamental frequency given by the following equivalent inductance and capacitance.

$$f = \frac{2\pi}{\sqrt{LC}}$$

The microplasma source 100 is designed to minimize undesirable resonances that are caused by parasitic elements, intercoil capacitances, and coupling to other structures. The matching elements are chosen using known techniques. Tunable reactive elements may be used to provide an impedance match. Frequency adjustments in the RF signal can also be used to provide an impedance match. Frequency adjustments can be implemented using a control circuit (not shown) that optimizes the frequency used for plasma initiation and changes the frequency to an optimum operating frequency based on detected plasma emissions.

In one embodiment, the resonant frequency of the resonant antenna structure 102 is in the frequency range of about 100–1,500 MHz. The skin effects in the resonant antenna structure 102 becomes significant in this frequency range. The material and the geometry of the resonant antenna structure 102 can be optimized to preserve the Q-value of the resonant antenna structure 102. Preserving the Q-value lowers the energy losses per cycle and maximizes the energy transfer and field strength. An upper limit of the resonant frequency is determined by the electron/neutral collision rate in the plasma.

Figure 2:
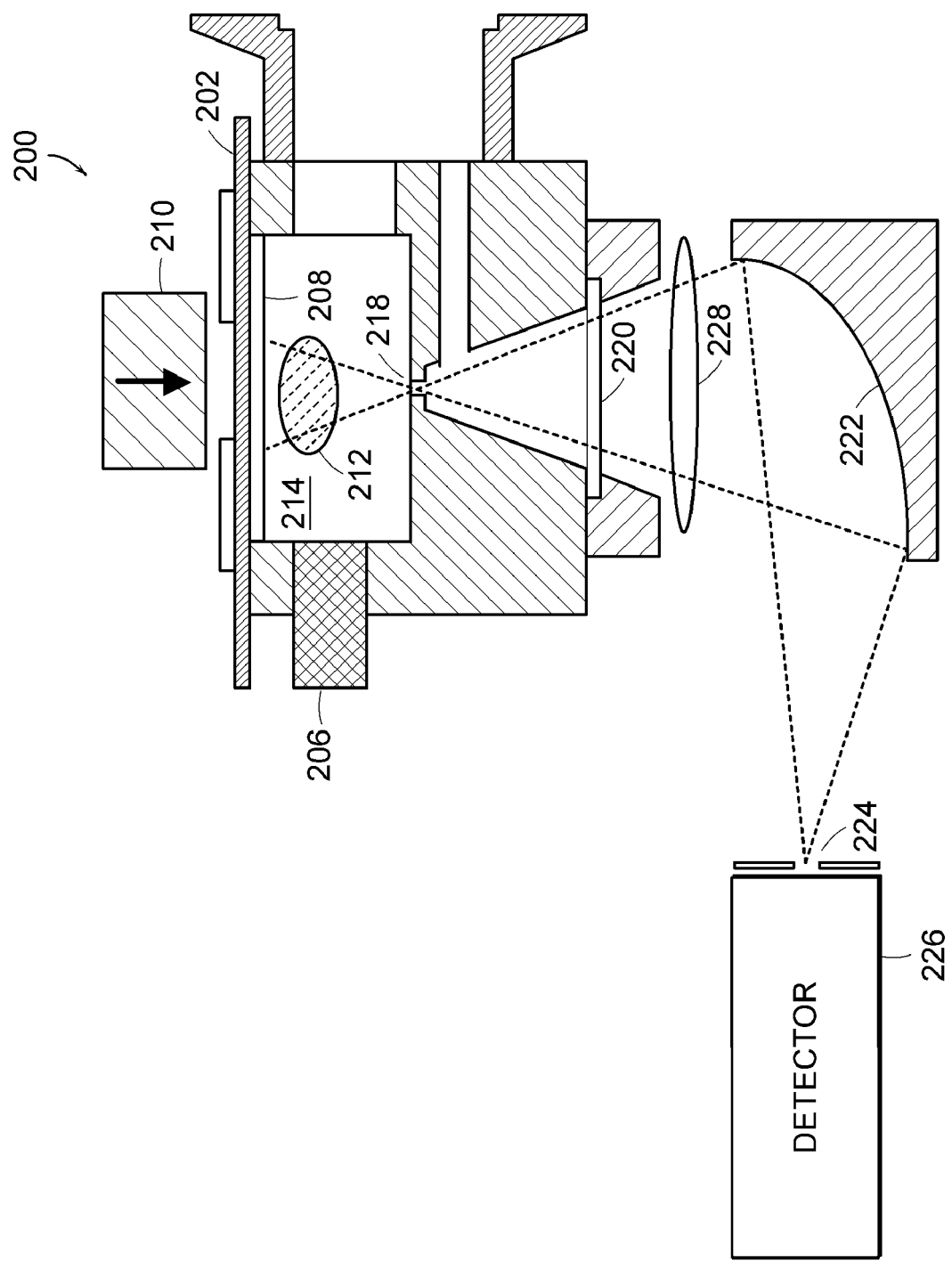
FIG. 2 is a block diagram of a cross section of a microplasma emission spectrometer according to the present invention.

FIG. 2 illustrates a block diagram of a cross section of a microplasma emission spectrometer 200 according to the present invention. The microplasma emission spectrometer 200 includes a microplasma source 202, such as the microplasma source 100 that was described in connection with FIG. 1.

Other microplasma sources, such as the inductively coupled microplasma source, that is described in U.S. Pat. No. 5,942,855 to Hopwood, and the ring resonator source that is described U.S. Patent Application Ser. No. 60/436,982 to Hopwood, can be used. In general, any source with a highly efficient resonant structure can be used.

The system utilizes a microplasma source 202 that generates a relatively small volume microplasma. In one embodiment, the plasma volume is approximately 1 cm$^3$ and the sheath width is about 1 mm. In this embodiment, the plasma has a plasma sheath volume-to-total plasma volume ratio that is approximately 0.5. The power density is in the range of between about 1–10 W/cm$^3$ when the RF signal has a power that is in the range of between about 1–10 W.

The microplasma source 202 includes a high-efficiency resonant antenna structure. In one embodiment, the resonant antenna structure 102 (FIG. 1) is an electrode-less microplasma source. Electrode-less microplasma sources do not use high electrical potentials and thus are not susceptible to damage caused by sputtering, etching, and arcing.

The resonant antenna structure can be the resonant antenna structure 102 described in connection with FIG. 1 with 0.015 in (0.375 mm) lines and spaces and with a 5 mm to 15 mm diameter. Such a resonant antenna structure exhibits stable single-frequency operation without self-resonant effects when tuned at frequencies in the range of about 230–250 MHz. Stable frequency operation may eliminate mode-hopping effects.

The microplasma source 202 also includes impedance matching components and the amplifiers (not shown) that are described in connection with FIG. 1. In addition, the microplasma source 202 includes a DC power input (not shown) that is connected to a DC power supply. RF energy that is used to excite the plasma may enter through a connector, such as a slide-in mating type mechanism. Such connectors make reproducible low-loss connections. A "card-edge" connector, coaxial or other connector that are well known in the industry can also be used. In other embodiments, the RF energy is generated by an oscillator in the microplasma source as described in connection with FIG. 1.

A plasma igniter 206, such as an ignition electrode that generates an arc or electron spray into the plasma chamber or an UV radiation source that introduces UV radiation into the chamber, can be used to initially ignite the plasma.

A window 208 is positioned over the top of the resonant antenna structure (which is facing down in FIG. 2) in the microplasma source 202. The window 208 may be attached to the resonant antenna structure with an adhesive material or a mechanical claming structure.

In one embodiment, the microplasma emission spectrometer 200 includes a magnet 210 that is positioned adjacent to the microplasma source 202. The magnet can be any type of magnet, such as a permanent magnet or an electromagnet. The magnet 210 generates a magnetic field for confining a plasma 212 generated by the microplasma source 202.

A chamber 214 is positioned adjacent to the window 208. The chamber 214 is designed to contain a volume of gas for analysis and the plasma 212 that is formed from the volume of gas. The chamber 214 includes a gas inlet port through which a gas sample may enter. More than one port may be used to provide flow through the chamber 214. In some embodiments, the chamber 214 is coupled to a vacuum pump that evacuates the chamber so that the chamber 214 can be maintained at a sub-atmospheric pressure level in order to facilitate the introduction of the volume of gas for analysis.

Pressure control in the chamber 214 may also be provided by a system (not shown) interfacing with the microplasma spectrometer 200. The chamber 214 can be isolated using valves so that the gas sample is completely confined, or may be capable of gas exchange through diffusion, conduction or convective mechanisms. In the embodiment shown, the chamber 214 connects to a tubulation and connecting fitting.

The chamber 214 includes an exit aperture 218 that provides an outlet for emissions from the microplasma 212 generated in the chamber 214. In one embodiment, the exit aperture 218 is formed in a transmission window 220 that comprises the bottom of the chamber 214. In another embodiment, the exit aperture 218 is a separate element, such as a thin piece of foil, that is placed or attached to the bottom of the chamber 214. In another embodiment, the exit aperture 218 is machined directly into the chamber 214.

In yet another embodiment, the exit aperture 218 has a small open area that is remotely positioned relative to the transmission window 220. The small open area can reduce undesirable depositions on the transmission window 220. Increasing the spacing between the exit aperture 218 and the transmission window 220 will reduce the deposition rate at the transmission window 220. It is desirable to have the spacing be larger than a mean free path because the probability of scattering to a wall is increased. In one embodiment, deposition is decreased by using a high ratio of window area to exit aperture area. For example, a ratio of window area to exit aperture area that is equal to about ten will decrease the deposition rate by a factor of ten.

In one embodiment, the exit aperture 218 and transmission window 220 are dimensioned and positioned so that the combination subtends a large fraction of the microplasma 212 in order to maximize the optical emission flux that is imaged or transmitted through the transmission window 220. Maximizing the optical emission flux will improve the efficiency of the microplasma emission spectrometer 200.

The particular geometry of the exit aperture 218 that maximizes optical intensity depends upon the particular geometry of the resonant antenna structure of the microplasma source 202. The geometry of the exit aperture 218 that maximizes the optical emission flux from the microplasma source 202 can be a plane, a line, or a circle.

For example, a microplasma spectrometer has been constructed having an exit aperture forming a slit that is oriented perpendicular to a plane of a coil shaped antenna structure with the center point of the slit positioned in close proximity (2–5 mm) to the surface of the antenna structure. Experiments have shown that such an exit aperture passed a 50% larger portion of the optical emission flux from the microplasma 212 than one oriented parallel to the plane because the emission intensity was concentrated in a thin disk parallel to the antenna.

An optical transmission window 220 is positioned adjacent to the exit aperture 218 in the optical path of the optical emission flux from the microplasma 212. Collection optics 222 are positioned adjacent to the optical transmission window 220 in the optical path of the emission flux from the microplasma source 202. The collection optics 222 may include an additional lens 228 to focus the emission flux.

The collection optics 222 are used for collecting, refocusing, and transmitting the optical emission flux from the microplasma 212 to an entrance aperture 224 or focal plane of a spectrally sensitive detection system 226. The exit aperture 218, transmission window 220, and collection optics 222 together limit the portion of the plasma volume from which emissions may be collected.

For example, in one embodiment, the diameter of the transmission window 220 is about 0.5 cm and the exit aperture 218 is configured as a narrow slit having a width that is about 0.5 mm and a height that is about 2.5 mm. The transmission window 220 is located approximately 1 cm from the exit aperture 218. The center of the chamber 214 and the microplasma 212 are spaced a distance that is about 1 cm from the exit aperture 218. The resulting microplasma is approximately a cube with sides of length 1 cm. Ray-tracing methods can be used to calculate the fraction of the microplasma from which optical emission may be imaged or transmitted to the detector. In this example, the fraction is approximately one-eighth of the microplasma volume.

In another embodiment, the exit aperture 218, transmission window 220 and collection optics 222 are chosen so that emissions from at least one-quarter of a total volume of the microplasma are imaged or transmitted through the entrance aperture 224 of a spectrally sensitive detection system 226. In yet other embodiments, emissions from at least one-half of a total volume of the microplasma are imaged or transmitted through the entrance aperture 224.

In one embodiment, the entrance aperture 224 of the spectrally sensitive optical detection system 226 is butt-coupled to the exit aperture 218 of the chamber 214. In this embodiment, the microplasma subtends substantially all of the acceptance cone of the entrance aperture 224. The dimensions of the exit aperture 218 are chosen so that they do not substantially limit the emissions accepted by the spectrally sensitive detection system 226.

The spectrally sensitive detection system 226 can be any of numerous types of optical detection systems. For example, the spectrally sensitive optical detection system 226 can be a spectrometer, a detector array, a monochromator based spectrometer, or one or more single wavelength detectors, such as a filter and photodiode.

The microplasma source of the present invention consumes relatively little power, allowing the power supply, plasma source 202, and spectrally sensitive detector 226 to be in close proximity in a miniaturized package. Maintaining a relatively low temperature at the spectrally sensitive detector 226 is desirable to limit thermal noise. In one embodiment, the microplasma source 202 is thermally isolated from the spectrally sensitive detector 226. In another embodiment the spectrally sensitive detector 226 is actively cooled. In some embodiments less than 20 W are consumed by the plasma source, allowing the use of passive cooling.

In one embodiment, the spectrally sensitive optical detection system 226 is a spectrometer. The entrance aperture 224 can be the entrance slit of the spectrometer and the chamber 214 can be directly integrated into the spectrometer. The entrance aperture 224 dimensions can be chosen to optimize spectrometer performance based upon resolution and throughput. In one embodiment, the width of the exit aperture 218 is slightly wider than the entrance slit of the spectrometer so as to simplify alignment of the microplasma source 202 to the spectrometer. The chamber 214 is temperature controlled in some embodiments in order to maintain optical alignment tolerances and/or to reduce coating of the interior surfaces.

Figure 3:
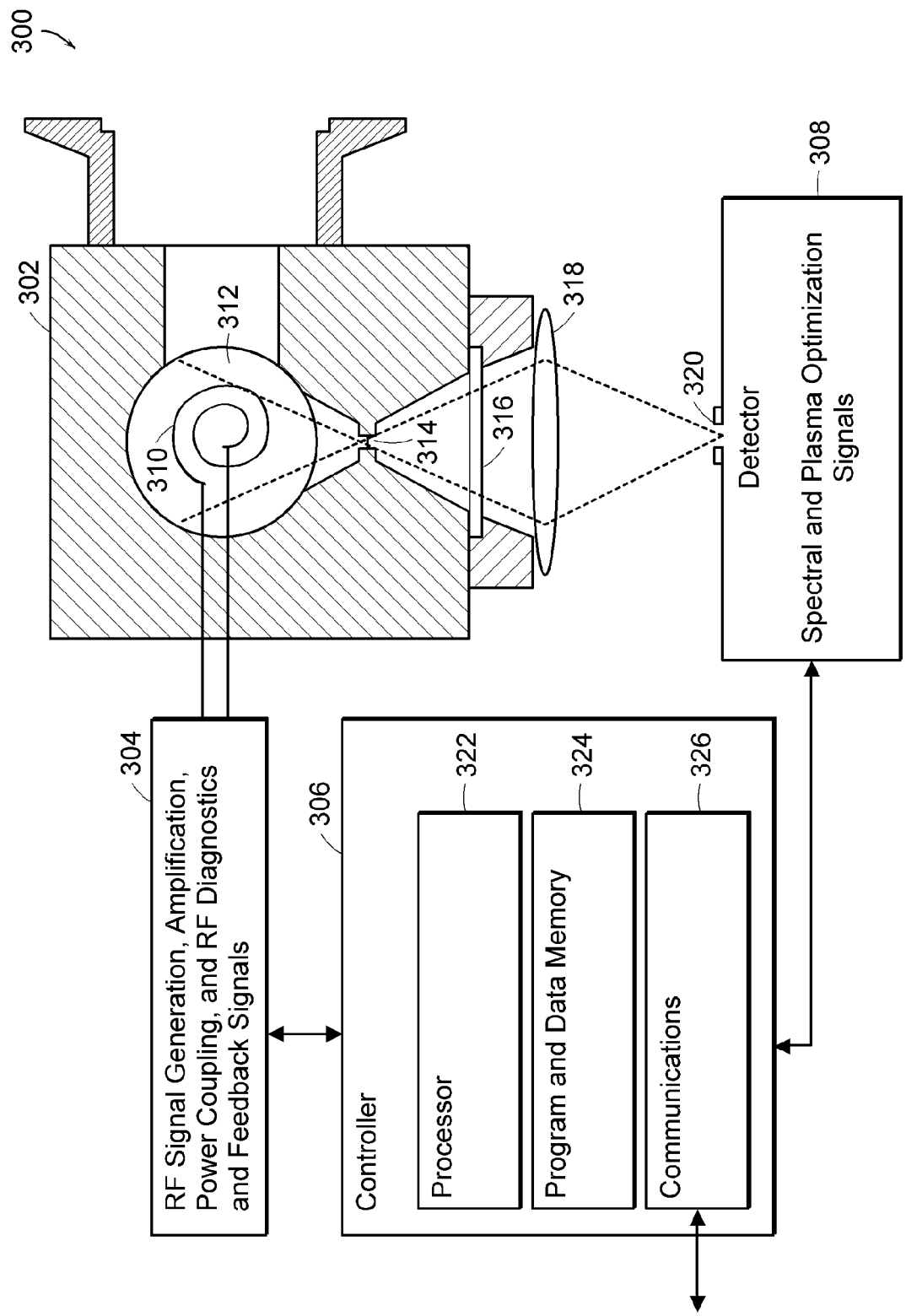
FIG. 3 is a block diagram of a microplasma emission spectrometer according to the present invention illustrating a top view of a microplasma source connected to a power supply and to control system.

FIG. 3 is a block diagram of a microplasma emission spectrometer 300 according to the present invention illustrating a top view of a microplasma source 302 that is connected to a power supply 304, a control system 306, and a spectrally sensitive detector 308. The top view of the microplasma source 302 shows a spiral resonant antenna structure 310 that is positioned in proximity to a chamber 312.

In some embodiments, the spiral antenna structure 310 is self resonant. In other embodiments, the spiral antenna structure 310 is resonant with a separate reactive element. The antenna structure 310 can be formed in numerous other shapes, such as a square spiral shape or a helical shape. The spiral resonant antenna structure 310 is electrically connected to the power supply 304. The power supply 304 supplies a RF signal to the spiral resonant antenna structure 310 that generates the plasma.

The microplasma emission spectrometer 300 illustrates an exit aperture 314 that provides an outlet for emissions from the microplasma generated in the chamber 312. An optical transmission window 316 is positioned adjacent to the exit aperture 314 in the optical path of the optical emission flux from the microplasma source 302. Collection optics 318 are used to focus the emission flux onto an entrance slit 320 of the spectrally sensitive detector 308.

The control system 306 is electrically connected to the power supply 304 and to the spectrally sensitive detector 308. The control system 306 includes a processor 322 that executes programs which control the operation of the microplasma emission spectrometer 300 and which performs the necessary data acquisition and data reduction algorithms. For example, the programs can include programs that control the microplasma emission source including initiation, optimization, and terminating of the plasma discharge based either on an operator input or a control input from an external system. The programs may also control the spectrally sensitive detector and implement initialization, background subtraction, normalization, linearization and other algorithms.

The programs can also include measurement and data analysis algorithms, such as algorithms to calculate the line or spectral region intensities and intensity ratios, as well as higher order functions, such as correlation matrix calculations. The programs can also perform principle component analysis or partial least squares or similar algorithms that determine identification based on response or component libraries.

At least one communication interface 326 receives data from and sends instructions to the power supply 304 and to the spectrally sensitive detector 308. The at least one interface 326 also implements communications with operators or systems that are external to the microplasma emission spectrometer. The at least one communication interface 326 can be an analog, digital or a standard digital communications interface, such as RS232 or TCP/IP interface.

The communication interface 326 can accept control and configuration signals and can transmit status, raw and reduced data and control information. The communication interface 326 facilitates integration of the microplasma emission spectrometer 300 with other systems and facilitates automation. In one embodiment, the microplasma emission spectrometer 300 is integrated into a manufacturing tool and accepts control signals from the control system of the manufacturing tool.

In many industrial and environmental applications it is desirable to use a control system 306 that is integrated into the microplasma spectrometer 300 rather than using a dedicated computer. In one embodiment, the control system 306 is an embedded controller or other type of a miniaturized embedded controller that includes program memory, data memory, and input and output interfaces. Program and data memory 324 store the spectrometer control programs and the acquired data.

One aspect of the present invention is that the microplasma generated by a microplasma spectrometer according to the present invention can have a large plasma sheath volume-to-total plasma volume ratio. In some embodiments, the plasma sheath volume-to-total plasma volume ratio can be greater than about 0.1.

The plasma sheath thickness can be calculated in several ways. See, for example, Lieberman and Lichtenberg, "Principles of Plasma Discharges and Materials Processing", Wiley, 1994. For example, a plasma having a density that is equal to $10^{10}/cm^{-3}$ and an electron temperature of 4 eV will have a Debye length that is about 0.15 mm. The width of the plasma sheath will typically be between about 10 and 100 Debye lengths, which corresponds to a width that is between about 1–10 mm.

The volume of the plasma sheath can be expressed as the product of the width of the plasma sheath and the surface area of the plasma. The plasma volume can be modeled by a spherical plasma volume with a thin plasma sheath on the outer surface of the plasma. The plasma sheath volume-to-total volume ratio can be expressed as $R_{sv}=3s/r$, where s is the plasma sheath thickness and r is the radius of the plasma. The ratio may change somewhat for other plasma shapes.

For example, a 1 cm³ microplasma (r=6.2 mm) with a 1 mm sheath has a plasma sheath volume-to-total volume ratio that is approximately one-half. The plasma sheath volume-to-total volume ratio decreases as the microplasma becomes larger. As the microplasma becomes smaller, the plasma sheath volume-to-total volume ratio increases until the sheath begins to consume the plasma entirely. In the limit where the plasma sheath begins to consume the plasma entirely, the emission intensity decreases. In one embodiment of the present invention, the plasma sheath volume-to-total volume ratio is in the range of approximately 0.1 to 0.9.

In some embodiments of the microplasma spectrometer, a relatively high sheath-to-volume ratio is desirable because such a spectrometer can have a relatively small footprint and low overall power requirements. Spectrometers having smaller footprints will require much less total power to operate because the power consumption of the entire system is largely determined by the plasma emission source. Having relatively low power requirements enables portability. In addition, the optical system of the microplasma spectrometer can be designed to sample a much larger fraction of the total optical emission generated as this ratio increases. Additionally, low power operation reduces thermal dissipation and heating of other system components.

In some embodiments it may be desirable to decrease the sheath volume-to-total volume ratio. In these embodiments, miniaturization is usually desired and the microplasma dimensions are fixed by other constraints. The sheath width can be decreased by increasing the density of the microplasma or by increasing the power level. The plasma sheath volume-to-total volume ratio also depends upon the magnitude of the magnetic field experienced by the plasma. The magnetic field can also decrease the sheath volume-to-total volume ratio because the magnetic field confines the plasma and increases the plasma density.

The sheath volume-to-total volume ratio is a fundamental metric of microplasma systems. A microplasma source with a sheath volume-to-total volume ratio that is in the range of 0.1 to 0.9 can result in a microplasma source having desirable operating characteristics and having desirable physical characteristics, such as small physical size, low power consumption, and high thermal dissipation.

FIG. 4 illustrates various magnetic field configurations that provide magnetic field enhancements to the microplasma source. Magnetic field enhancements are particularly useful for microplasma sources. For example, the pressure range of known micro ICP sources reported in the literature is between about 50 mTorr to 10,000 mTorr. However, there are many applications where microplasma based sensors need to operate in the 0.5–50 mTorr pressure range.

Experiments have shown that applying a magnetic field to a microplasma spectrometer according to the present invention will increase the emission intensity by a factor of two or more and that microplasmas can be sustained with lower operating pressures that are less than 1 mTorr. Increasing the emission intensity will increase the signal-to-noise ratio of the system. Low pressure operation is important for microplasma spectrometers because some spectroscopy applications require operation at gas pressures that are as low as 1 mTorr. In addition, experiments have shown that microplasmas can be initiated at lower pressure if a magnetic field is present.

The magnetic field generated by the magnet 210 (FIG. 2) confines the electrons by constraining the diffusional transport perpendicular to the field lines and by forming a magnetic mirror with spatially varying magnetic field strengths (cusps). These effects are well known in plasma systems with dimensions that are much larger that the electron gyroradius. However, these effects were not expected to be seen in microplasmas sources with small dimensions. The particular magnetic field configuration is an important factor in achieving magnetic field enhancements.

In FIGS. 4A–F the relative position of the resonant antenna structure 102 (FIG. 1) is indicated by the cross hatched box. FIG. 4A illustrates a cusp magnetic field configuration that provided relatively little magnetic field enhancement. FIG. 4B illustrates a converging magnetic field configuration that provides moderate magnetic field enhancement (about 20%). FIG. 4C illustrates a uniform magnetic field configuration that also provides moderate magnetic field enhancement (about 20%). FIG. 4D illustrates a tangential magnetic field configuration that also provides moderate magnetic field enhancement (about 20%).

FIGS. 4E and 4F illustrates magnetic field configuration that provide higher magnetic field enhancement. FIG. 4E illustrates a diverging magnetic field configuration that provides relatively high magnetic field enhancement (about 50%). FIG. 4F illustrates a "barrel"-type magnetic field configuration that provides high magnetic field enhancement (greater than 80%). The "barrel"-type magnetic field configuration will minimize wall losses for a cylindrical chamber with a diameter-to-height ratio that is approximately equal to one. These effects have been observed at pressures from about 1 mTorr to greater than 100 mTorr.

The magnetic field generated by the magnet 210 (FIG. 2) can also be used to improve the coupling of electromagnetic energy between the antenna and microplasma. Electron cyclotron resonance coupling between electromagnetic waves and a plasma is well known in the art for long wavelength conditions (2.45 GHz or about 10 cm) and relatively large volume plasmas (~20–60 cm diameter). Microplasma sources generally have much smaller system dimensions, so a different wave coupling theory must be applied to understand the ECR condition. The geometry of the chamber 214 (FIG. 2) and the geometry of the resonant antenna structure 102 (FIG. 1) can be designed so that the electron motion and antenna near field RF fields are in resonance at a particular frequency.

For example, the ECR resonance condition at 2.45 GHz occurs when the magnetic field is approximately 880 Gauss. The ECR resonance condition at a frequency of 600 MHz occurs when the magnetic filed is approximately 220 Gauss. These field strengths are easily achieved with inexpensive permanent magnets, and are within the range of the resonant antenna structure 102 (FIG. 1) described in connection with FIG. 1.

EQUIVALENTS

While the invention has been particularly shown and described with reference to specific preferred embodiments, it should be understood by those skilled in the art that various changes in form and detail may be made therein without departing from the spirit and scope of the invention as defined herein.

What is claimed is:

1. A microplasma emission spectrometer comprising:
   a chamber for confining a sample volume of gas, the chamber having an exit aperture and a window that passes optical emission;
   a microplasma source having a resonant antenna structure that is positioned proximate to the chamber, the resonant antenna structure generating a microplasma in the chamber from the sample volume of gas;
   a RF power supply that is electrically coupled to the resonant antenna structure, the RF power supply providing power to the resonant antenna structure that generates the microplasma from the sample volume of gas; and
   a spectrally sensitive detector having an entrance that is optically coupled to the microplasma, the entrance having dimensions and being positioned so that emissions from at least one-tenth of a total volume of the microplasma are transmitted through the entrance of the spectrally sensitive detector.

2. The spectrometer of claim 1 wherein the microplasma source is formed on a planar substrate.

3. The spectrometer of claim 2 wherein the planar substrate is chosen from the group consisting of glass, sapphire, quartz, aluminum nitride, alumina, fused silica, fiberglass, fiber reinforced epoxy, FR-4, Teflon (PTFE), delrin, polyimide, ceramics, and ceramic/polymer composites.

4. The spectrometer of claim 2 wherein the microplasma source is fabricated monolithically on the planar substrate.

5. The spectrometer of claim 2 further comprising a discrete electrical element that is attached to the planar substrate.

6. The spectrometer of claim 1 wherein the entrance of the spectrally sensitive detector has dimensions and is positioned so that emissions from at least one-quarter of a total volume of the microplasma are transmitted through the entrance of the spectrally sensitive detector.

7. The spectrometer of claim 1 wherein the entrance of the spectrally sensitive detector is butt coupled to the window.

8. The spectrometer of claim 1 wherein the microplasma source generates a microplasma having a plasma sheath volume-to-total plasma volume ratio that is greater than about 0.1.

9. The spectrometer of claim 1 wherein the power provided by the RF power supply is less than about 20 W and a power density of the microplasma is greater than about 0.5 $W/cm^3$.

10. The spectrometer of claim 1 wherein the resonant antenna structure is driven at a frequency that is in the range of 100–1,500 MHz.

11. The spectrometer of claim 1 wherein the resonant antenna structure comprises a spiral antenna structure.

12. The spectrometer of claim 1 wherein the resonant antenna structure is formed of a material selected from the group consisting of gold, copper, platinum, aluminum, nickel, electro-less nickel, silver, tin, and solder material.

13. The spectrometer of claim 1 further comprising a magnet that is positioned relative to the resonant antenna structure so that a magnetic field generated by the magnet confines electrons in the microplasma.

14. The spectrometer of claim 13 wherein a magnitude of the magnetic field generated by the magnet is chosen to create an electron cyclotron resonance condition at one or more points within the chamber at a frequency of a signal provided by the RF power supply.

15. The spectrometer of claim 1 wherein the spectrally sensitive detector comprises an optical spectrometer.

16. The spectrometer of claim 1 further comprising an optical element that focuses emissions from the microplasma onto the entrance of the spectrally sensitive detector.

17. The spectrometer of claim 1 wherein the exit aperture of the chamber has a width that is less than one mean free path of a gaseous species of interest in the microplasma.

18. The spectrometer of claim 1 wherein a distance between the window and the exit aperture of the chamber is greater than about one mean free path of a gaseous species of interest in the microplasma.

19. The spectrometer of claim 1 wherein an area of the exit aperture is less than about ten times an area of the window.

20. A method of analyzing a gaseous environment, the method comprising:
   introducing a volume of gas to be analyzed into a chamber;
   generating a microplasma from the volume of gas;
   imaging emissions generated within at least one-tenth of a total volume of the microplasma onto an entrance of a spectrally sensitive detector; and
   analyzing at least one spectral region of the imaged emissions to characterize the gaseous environment.

21. The method of claim 20 wherein the imaging comprises imaging with an optical system.

22. The method of claim 20 wherein the introducing the volume of gas comprises introducing a volume of gas by diffusion.

23. The method of claim 20 wherein the introducing the volume of gas comprises introducing a volume of gas by establishing a pressure differential between the gaseous environment and the chamber.

24. The method of claim 20 further comprising controlling the pressure inside the chamber.

25. The method of claim 20 further comprising generating a magnetic field through the microplasma, the magnetic field confining electrons in the microplasma.

26. The method of claim 25 wherein a magnitude of the magnetic field is chosen to create an electron cyclotron resonance condition in the microplasma.

27. A microplasma spectrometer comprising:
- a chamber for confining a sample volume of gas, the chamber having an exit aperture and a window that passes emissions;
- a microplasma source that generates a microplasma from the sample volume of gas, the microplasma having a plasma sheath volume-to-total volume ratio that is approximately between about 0.1 and 0.9;
- an optical element that is positioned to image emissions from the microplasma, the optical element being positioned a distance from a center of the microplasma that is less than ten times a transverse dimension of the microplasma; and
- a spectrally sensitive detector coupled to the optical element.

28. The spectrometer of claim 27 wherein the microplasma source is formed on a planar substrate.

29. The spectrometer of claim 28 further comprising a discrete electrical element that is attached to the planar substrate.

30. The spectrometer of claim 28 wherein the microplasma source is fabricated monolithically on the planar substrate.

31. The spectrometer of claim 27 wherein a power consumed by the microplasma source is less than about 20 W.

32. The spectrometer of claim 27 wherein the microplasma source comprises a resonant antenna structure that is driven at a frequency in the range of about 100–1,500 MHz.

33. The spectrometer of claim 27 further comprising a magnet that is positioned relative to the microplasma source so that a magnetic field generated by the magnet confines electrons in the microplasma.

34. The spectrometer of claim 33 wherein a magnitude of the magnetic field generated by the magnet is chosen to create an electron cyclotron resonance condition at one or more points within the chamber.

35. The spectrometer of claim 27 wherein the optical element images emissions from the microplasma onto the entrance of the spectrally sensitive detector.

36. The spectrometer of claim 27 wherein the exit aperture of the chamber has a width that is less than one mean free path of a gaseous species of interest in the microplasma.

37. The spectrometer of claim 27 wherein a distance between the window and the exit aperture of the chamber is greater than one mean free path of a gaseous species of interest in the microplasma.

38. The spectrometer of claim 27 wherein an area of the exit aperture is less than about ten times an area of the window.

39. A microplasma spectrometer comprising:
- a means for introducing a volume of gas to be analyzed into a chamber;
- a means for generating a microplasma from the volume of gas, the microplasma having a plasma sheath volume-to-total plasma volume ratio that is greater than about 0.1;
- a means for imaging emissions generated by the microplasma to an entrance of a spectrally sensitive detector; and
- a means for analyzing at least one spectral region of the imaged emissions to characterize the gaseous environment.

* * * * *